United States Patent
Beihoffer et al.

[11] Patent Number: 6,072,101
[45] Date of Patent: Jun. 6, 2000

[54] MULTICOMPONENT SUPERABSORBENT GEL PARTICLES

[75] Inventors: Thomas W. Beihoffer, Arlington Heights; Michael A. Mitchell, Lake Zurich, both of Ill.

[73] Assignee: Amcol International Corporation, Arlington Heights, Ill.

[21] Appl. No.: 08/974,125

[22] Filed: Nov. 19, 1997

[51] Int. Cl.[7] .................................................. A61F 13/15
[52] U.S. Cl. ......................... 604/372; 604/368; 604/367; 604/385.1
[58] Field of Search .................................... 526/200, 240; 428/402; 424/487; 524/364, 35; 604/372, 368, 367, 385.1

[56] References Cited

U.S. PATENT DOCUMENTS

| | | |
|---|---|---|
| 3,041,292 | 6/1962 | Hatch . |
| 3,332,890 | 7/1967 | Hatch . |
| 3,645,922 | 2/1972 | Weiss et al. . |
| 3,716,481 | 2/1973 | Battaerd . |
| 3,957,698 | 5/1976 | Hatch . |
| 4,139,499 | 2/1979 | Wade et al. . |
| 4,206,051 | 6/1980 | Bolto et al. . |
| 4,229,545 | 10/1980 | Eppinger et al. . |
| 4,378,439 | 3/1983 | Pilkington . |
| 4,685,909 | 8/1987 | Berg et al. . |
| 4,818,598 | 4/1989 | Wong . |
| 5,026,800 | 6/1991 | Kimura et al. ........................... 526/200 |
| 5,085,787 | 2/1992 | Pinschmidt, Jr. et al. . |
| 5,274,018 | 12/1993 | Tanaka et al. . |
| 5,409,771 | 4/1995 | Dahmen et al. . |
| 5,447,727 | 9/1995 | Graham ................................... 424/487 |
| 5,669,894 | 9/1997 | Goldman et al. . |
| 5,716,707 | 2/1998 | Mukaida et al. ......................... 428/402 |
| 5,849,862 | 12/1998 | Davies et al. . |

FOREIGN PATENT DOCUMENTS

| | | |
|---|---|---|
| 2066010 | 10/1992 | Canada . |
| 0 700 672 | 3/1996 | European Pat. Off. . |
| 43 33 056 | 3/1995 | Germany . |
| WO 96/15163 | 5/1996 | WIPO . |
| WO 96/15180 | 5/1996 | WIPO . |
| WO 96/17681 | 6/1996 | WIPO . |
| WO 98/24832 | 6/1998 | WIPO . |
| WO 98/37149 | 8/1998 | WIPO . |

OTHER PUBLICATIONS

Bolto et al., "Further rapidly reacting ion–exchange resins," *J. Polymer Sci.*, Symposium No. 55, 87–94 (1976).

*Primary Examiner*—John G. Weiss
*Assistant Examiner*—Miley C. Peppers, III
*Attorney, Agent, or Firm*—Marshall, O'Toole, Gerstein, Murray & Borun

[57] ABSTRACT

Multicomponent superabsorbent gel particles are disclosed. The multicomponent particles comprise at least one acidic water-absorbing resin and at least one basic water-absorbing resin. Each particle contains microdomains of the acidic resin and/or the basic resin homogeneously dispersed throughout the particle.

85 Claims, 1 Drawing Sheet

MULTICOMPONENT SUPERABSORBENT GEL PARTICLES

FIELD OF THE INVENTION

The present invention relates to multicomponent superabsorbent gel particles containing at least one acidic water-absorbing resin and at least one basic water-absorbing resin. Each superabsorbent gel particle has microdomains of the acidic resin and/or basic resin homogeneously dispersed throughout the gel particle.

BACKGROUND OF THE INVENTION

Water-absorbing resins are widely used in sanitary goods, hygienic goods, wiping cloths, water-retaining agents, dehydrating agents, sludge coagulants, disposable towels and bath mats, disposable door mats, thickening agents, disposable litter mats for pets, condensation-preventing agents, and release control agents for various chemicals. Water-absorbing resins are available in a variety of chemical forms, including substituted and unsubstituted natural and synthetic polymers, such as hydrolysis products of starch acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines, and polyacrylonitriles.

Such water-absorbing resins are termed "superabsorbent polymers," or SAPs, and typically are lightly crosslinked hydrophilic polymers. SAPs are generally discussed in Goldman et al. U.S. Pat. No. 5,669,894. SAPs can differ in their chemical identity, but all SAPs are capable of absorbing and retaining amounts of aqueous fluids equivalent to many times their own weight, even under moderate pressure. For example, SAPs can absorb one hundred times their own weight, or more, of distilled water. The ability to absorb aqueous fluids under a confining pressure is an important requirement for an SAP used in a hygienic article, like a diaper.

The dramatic swelling and absorbent properties of SAPs are attributed to (a) electrostatic repulsion between the charges along the polymer chains, and (b) osmotic pressure of the counter ions. It is known, however, that these absorption properties are drastically reduced in solutions containing electrolytes, such as saline, urine, and blood. The polymers do not function as effective SAPs in the presence of such physiologic fluids.

The decreased absorbency of electrolyte-containing liquids is illustrated by the absorption properties of a typical, commercially available SAP, i.e., sodium polyacrylate, in deionized water and in 0.9% by weight sodium chloride (NaCl) solution. The sodium polyacrylate can absorb 146.2 grams (g) of deionized water per gram of SAP (g/g) at 0 psi (g/g), 103.8 g of deionized water per gram of polymer at 0.28 psi, and 34.3 g of deionized water per gram of polymer of 0.7 psi. In contrast, the same sodium polyacrylate is capable of absorbing only 43.5 g, 29.7 g, and 24.8 g of 0.9% aqueous NaCl at 0 psi, 0.28 psi, and 0.7 psi, respectively. The absorption capacity of SAPs for body fluids, like urine or menses, therefore, is dramatically lower than for deionized water because such fluids contain electrolytes. This dramatic decrease in absorption is termed "salt poisoning."

The salt poisoning effect has been explained as follows. Water-absorption and water-retention characteristics of SAPs are attributed to the presence of ionizable functional groups in the polymer structure. The ionizable groups typically are carboxyl groups, a high proportion of which are in the salt form when the polymer is dry, and which undergo dissociation and solvation upon contact with water. In the dissociated state, the polymer chain contains a plurality of functional groups having the same electric charge and, thus, repel one another. This electronic repulsion leads to expansion of the polymer structure, which, in turn, permits further absorption of water molecules. Polymer expansion, however, is limited by the crosslinks in the polymer structure, which are present in a sufficient number to prevent solubilization of the polymer.

It is theorized that the presence of a significant concentration of electrolytes interferes with dissociation of the ionizable functional groups, and leads to the "salt poisoning" effect. Dissolved ions, such as sodium and chloride ions, therefore, have two effects on SAP gels. The ions screen the polymer charges and the ions eliminate the osmotic imbalance due to the presence of counter ions inside and outside of the gel. The dissolved ions, therefore, effectively convert an ionic gel into a nonionic gel, and swelling properties are lost.

The most commonly used SAP for absorbing electrolyte-containing liquids, like urine, is neutralized polyacrylic acid, i.e., containing at least 50%, and up to 100%, neutralized carboxyl groups. Neutralized polyacrylic acid, however, is susceptible to salt poisoning. Therefore, to provide an SAP that is less susceptible to salt poisoning, either an SAP different from neutralized polyacrylic acid must be developed, or the neutralized polyacrylic acid must be modified or treated to at least partially overcome the salt poisoning effect.

The removal of ions from electrolyte-containing solutions is often accomplished using ion exchange resins. In this process, deionization is performed by contacting an electrolyte-containing solution with two different types of ion exchange resins, i.e., an anion exchange resin and a cation exchange resin. The most common deionization procedure uses an acid resin (i.e., cation exchange) and a base resin (i.e., anion exchange). The two-step reaction for deionization is illustrated with respect to the desalinization of water as follows:

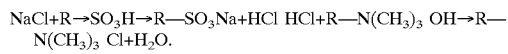

The acid resin (R—$S_3$H) removes the sodium ion; and the base resin (R—N(CH$_3$)$_3$OH) removes the chloride ions. This ion exchange reaction, therefore, produces water as sodium chloride is adsorbed onto the resins.

The most efficient ion exchange occurs when strong acid and strong base resins are employed. However, weak acid and weak base resins also can be used to deionize saline solutions. The efficiency of various combinations of acid and base exchange resins are as follows:

Strong acid—strong base (most efficient)
Weak acid—strong base
Strong acid—weak base
Weak acid—weak base (least efficient).

The weak acid/weak base resin combination requires that a "mixed bed" configuration be used to obtain deionization. The strong acid/strong base resin combination does not necessarily require a mixed bead configuration to deionize water. Deionization also can be achieved by sequentially passing the electrolyte-containing solution through a strong acid resin and strong base resin.

A "mixed bed" configuration is simply a physical mixture of an acid ion exchange resin and a base ion exchange resin in an ion exchange column, as disclosed in Battaerd U.S. Pat. No. 3,716,481. Other patents directed to ion exchange resins having one ion exchange resin imbedded in a second ion exchange resin are Hatch U.S. Pat. No. 3,957,698, Wade et al. U.S. Pat. No. 4,139,499, Eppinger et al. U.S. Pat. No. 4,229,545; and Pilkington U.S. Pat. No. 4,378,439. Composite ion exchange resins also are disclosed in Hatch U.S. Pat. Nos. 3,041,092 and 3,332,890, and Weiss U.S. Pat. No. 3,645,922.

The above patents are directed to nonswelling resins that can be used to remove ions from aqueous fluids, and thereby provide purified water. Ion exchange resins used for water purification must not absorb significant amounts of water because resin swelling resulting from absorption can lead to bursting of the ion exchange containment column.

Ion exchange resins or fibers also have been disclosed for use in absorbent personal care devices (e.g., diapers) to control the pH of fluids that reach the skin, as set forth in Berg et al., U.S. Pat. No. 4,685,909. The ion exchange resin is used in this application to reduce diaper rash, but the ion exchange resin is not significantly water absorbent and, therefore, does not improve the absorption and retention properties of the diaper.

Ion exchange resins having a composite particle containing acid and base ion exchange particles embedded together in a matrix resin, or having acid and base ion exchange particles adjacent to one another in a particle that is free of a matrix resin is disclosed in B. A. Bolto et al., *J. Polymer Sci.:— Symposium No. 55*, John Wiley and Sons, Inc. (1976), pages 87–94. The Bolto et al. publication is directed to improving the reaction rates of ion exchange resins for water purification and does not utilize resins that absorb substantial amounts of water.

Other investigators have attempted to counteract the salt poisoning effect and thereby improve the performance of SAPs with respect to absorbing electrolyte-containing liquids, such as menses and urine. For example, Tanaka et al. U.S. Pat. No. 5,274,018 discloses an SAP composition comprising a swellable hydrophilic polymer, like polyacrylic acid, and an amount of an ionizable surfactant sufficient to form at least a monolayer of surfactant on the polymer. In another embodiment, a cationic gel, like a gel containing quaternized ammonium groups and in the hydroxide (i.e., OH) form, is admixed with an anionic gel (i.e., a polyacrylic acid) to remove electrolytes from the solution by ion exchange. Quaternized ammonium group in the hydroxide form are very difficult and time-consuming to manufacture, thereby limiting the practical use of such cationic gels.

Wong U.S. Pat. No. 4,818,598 discloses the addition of a fibrous anion exchange material, like DEAE cellulose, to a hydrogel, like a polyacrylate, to improve absorption properties. The ion exchange resin "pretreats" the saline solution (e.g., urine) as the solution flows through an absorbent structure (e.g., a diaper). This pretreatment removes a portion of the salt from the saline. The conventional SAP present in the absorbent structure then absorbs the treated saline more efficiently than untreated saline. The ion exchange resin, per se, does not absorb the saline solution, but merely helps overcome the "salt poisoning" effect.

WO 96/17681 discloses admixing discrete anionic SAP particles, like polyacrylic acid, with discrete polysaccharide-based cationic SAP particles to overcome the salt poisoning effect. Similarly, WO 96/15163 discloses combining a cationic SAP having at least 20% of the functional groups in a basic (i.e., OH) form with a cationic exchanger resin, i.e., a nonswelling ion exchange resin, having at least 50% of the functional groups in the acid form. WO 96/15180 discloses an absorbent material comprising an anionic SAP, e.g., a polyacrylic acid and an anion exchange resin, i.e., a nonswelling ion exchange resin.

These references disclose combinations that attempt to overcome the salt poisoning effect.

However, the references merely teach the admixture of two types of particles, and do not suggest a single particle containing individual microdomains of an acidic resin and/or a basic resin. It would be desirable to provide discrete SAP particles that exhibit exceptional water absorption and retention properties, especially with respect to electrolyte-containing liquids, and thereby overcome the salt poisoning effect.

SUMMARY OF THE INVENTION

The present invention is directed to multicomponent SAPs comprising at least one acidic water-absorbing resin, like a polyacrylic acid, and at least one basic water-absorbing resin, like a poly(dialkylaminoalkyl acrylamide) or a poly(dialkylaminoalkyl methacrylamide), hereafter collectively referred to as poly(dialkylaminoalkyl (meth) acrylamides).

More particularly, the present invention is directed to multicomponent SAP particles containing discrete microdomains of at least one acidic water-absorbing resin and/or at least one basic water-absorbing resin homogeneously dispersed throughout the particle. The acidic resin can be a strong or a weak acidic resin. Similarly, the basic resin can be a strong or a weak basic resin. A preferred SAP contains microdomains of at least one weak acidic resin and/or at least one weak base resin.

Accordingly, one aspect of the present invention is to provide SAP particles that overcome the salt poisoning effect and demonstrate an improved ability to absorb and retain electrolyte-containing liquids, like saline, blood, urine, and menses.

Another aspect of the present invention is to provide an SAP having improved absorption and retention properties compared to a conventional SAP, like sodium polyacrylate. The present SAP particles are produced, for example, by coextruding an acidic water-absorbing hydrogel and a basic water-absorbing hydrogel to provide multicomponent SAP particles having a plurality discrete microdomains of an acidic resin and a basic resin dispersed throughout the particle. Such SAP particles demonstrate improved absorption and retention properties compared to SAP compositions comprising a simple admixture of acidic resin particles and basic resin particles.

In accordance with another important aspect of the present invention, the present multicomponent SAP particles also can be prepared by admixing dry particles of a basic resin with a hydrogel of an acidic resin, then extruding the resulting mixture to form multicomponent SAP particles having microdomains of a basic resin dispersed throughout a continuous phase of an acidic resin. Alternatively, dry acidic resin particles can be admixed with a basic resin hydrogel, followed by extruding the resulting mixture to form multicomponent SAP particles having microdomains of an acidic resin dispersed in a continuous phase of a basic resin. In addition, a multicomponent SAP particle containing microdomains of an acidic resin and a basic resin dispersed in a continuous phase of a matrix resin can be prepared by adding dry particles of the acidic resin and dry particles of the basic resin to a hydrogel of the matrix hydrogel, then extruding.

In accordance with yet another important aspect of the present invention, the acidic and basic resins are lightly crosslinked, such as with a suitable polyfunctional vinyl polymer. In preferred embodiments, the acidic resin, the basic resin, and/or the entire multicomponent SAP particle are surface treated to further improve water absorption and retention properties, especially under a load.

Yet another important feature of the present invention is to provide an SAP particle containing microdomains of a weak acidic water-absorbing resin and/or a weak basic water-absorbing resin. An example of a weak acid resin is polyacrylic acid having 0 to 20% neutralized carboxylic acid groups (i.e., DN=0 to DN=20). Examples of weak basic water-absorbing resins are a poly(vinylamine), a polyethylenimine, and a poly (dialkylaminoalkyl (meth) acrylamide) prepared from a monomer either having the general structure formula (I)

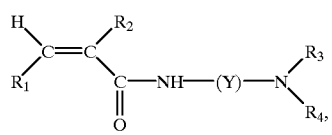

(I)

or the ester analog of (I) having the general structure formula (II)

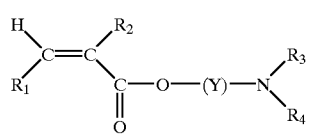

(II)

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms. An example of a strong basic water-absorbing resin is poly(vinylguanidine).

These and other aspects and advantages of the present invention will become apparent from the following detailed description of the preferred embodiments.

DETAILED DESCRIPTION OF THE PREFERRED EMBODIMENTS

The present invention is directed to multicomponent SAP particles containing microdomains of an acidic water-absorbing resin and/or a basic water-absorbing resin homogeneously dispersed throughout each particle. Each multicomponent SAP particle of the present invention contains at least one acidic water-absorbing resin and at least one basic water-absorbing resin. In one embodiment, the SAP particles consist essentially of acidic resins and basic resins, and contain microdomains of the acidic and/or basic resins. In another embodiment, microdomains of the acidic and basic resins are dispersed throughout an absorbent matrix resin.

The multicomponent SAP particles of the present invention are analogous to liquid emulsions wherein small droplets of a first liquid, i.e., the dispersed phase, are dispersed in a second liquid, i.e., the continuous phase. The first and second liquids are immiscible, and the first liquid, therefore, is homogeneously dispersed in the second liquid. The first liquid can be water or oil based, and conversely, the second liquid is oil or water based, respectively.

Figure 1:
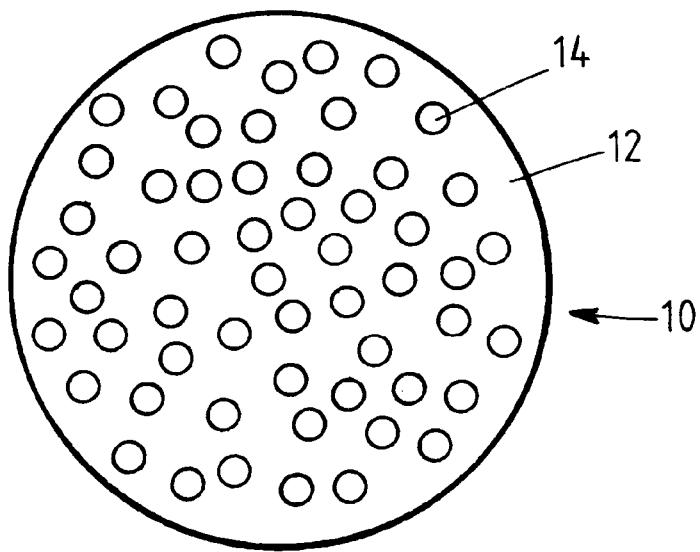
FIG. 1 is a schematic diagram of a water-absorbing particle containing microdomains of a first resin dispersed in a continuous phase of a second resin.

Therefore, in one embodiment, the multicomponent SAP particles of the present invention can be envisioned as microdomains of an acidic resin dispersed in a continuous phase of a basic resin, or as microdomains of a basic resin dispersed in a continuous acid resin. These multicomponent SAP particles are illustrated in FIG. 1 showing an SAP particle 10 having discrete microdomains 14 of a dispersed resin in a continuous phase of a second resin 12. If microdomains 14 comprise an acidic resin, then continuous phase 12 comprises a basic resin. Conversely, if microdomains 14 comprise a basic resin, then continuous phase 12 is an acidic resin.

Figure 2:
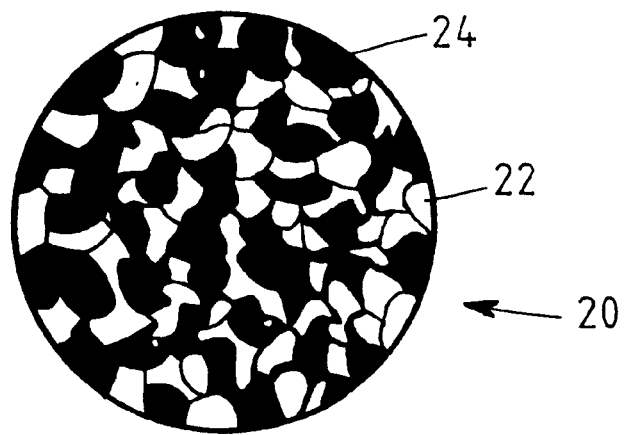
FIG. 2 is a schematic diagram of a water-absorbing particle containing microdomains of a first resin and microdomains of a second resin dispersed throughout the particle.

In another embodiment, the SAP particles are envisioned as microdomains of an acidic resin and microdomains of a basic resin dispersed throughout each particle, without a continuous phase. This embodiment is illustrated in FIG. 2, showing a multicomponent SAP particle 20 having a plurality of microdomains of an acidic resin 22 and a plurality of microdomains of a basic resin 24 dispersed throughout the particle.

In yet another embodiment, microdomains of the acidic and basic resins are dispersed throughout a continuous phase comprising a matrix resin. This embodiment also is illustrated in FIG. 1 wherein multicomponent SAP particle 10 contains microdomains 14 of acidic resin and basic resin dispersed in a continuous phase 12 of a matrix resin.

The multicomponent SAP particles of the present invention therefore comprise an acidic resin and a basic resin in a weight ratio of about 90:10 to about 10:90, and preferably about 20:80 to about 80:20. To achieve the full advantage of the present invention, the weight ratio of acidic resin to basic resin in a multicomponent SAP particle is about 30:70 to about 70:30.

The present multicomponent SAP particles contain at least about 50%, and preferably at least about 70%, by weight of acidic resin plus basic resin. To achieve the full advantage of the present invention, a multicomponent SAP particle contains about 80% to 100% by weight of the acidic resin plus basic resin. Components of the present SAP particles, other than the acidic and basic resin, typically, are matrix resins or other minor optional ingredients.

The multicomponent SAP particles of the present invention can be in any form, such as granules, fibers, beads, powders, flakes, or foams, or any other desired shape, such as a sheet of the multicomponent SAP. In embodiments wherein the multicomponent SAP is prepared using an extrusion step, the shape of the SAP is determined by the shape of the extrusion dye.

Preferably, the present SAP particles are in the form of a granule or a bead, having a particle size of about 10 to about 10,000 microns ($\mu$m), and preferably about 100 to about 1,000 $\mu$m. To achieve the full advantage of the present invention, the multicomponent SAP particles have a particle size of about 150 to about 800 $\mu$m.

Each multicomponent SAP particle contains a plurality of microdomains of an acidic water-absorbing resin and/or a basic water-absorbing resin. As illustrated hereafter, the microdomain structure of the present SAP particles provides improved water absorption and retention compared to an SAP comprising a simple mixture of discrete acidic SAP resin particles and basic SAP resin particles. The improved absorption and retention, especially of electrolyte-containing liquids, by the present multicomponent SAP particles, is attributed, in part, to the fact that electrolyte removal from the liquid is facilitated by contacting a single particle (which, in effect, performs an essentially simultaneous deionization of the liquid), as opposed to the liquid having to contact individual acidic and basic particles (which, in effect, performs a sequential two-step deionization). The following schematic reactions illustrate the reactions which occur to deionize, e.g., desalinate, an aqueous saline solution, and that are performed essentially simultaneously in a present microcomposite SAP particle, but are performed stepwise in a

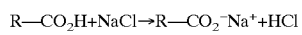

(acidic resin)

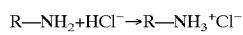

(basic resin)

simple mixture of acidic and basic resins.

The present multicomponent SAP particles, therefore, can be in a form wherein microdomains of an acidic water-absorbing resin are dispersed throughout a continuous phase of a basic water-absorbing resin. Alternatively, the multicomponent SAP can be in a form wherein microdomains of a basic resin are dispersed throughout a continuous phase of an acidic resin. In another embodiment, microdomains of one or more acidic resin and microdomains of one or more basic resin comprise the entire SAP particle, and neither type of resin is considered the dispersed or the continuous phase. In yet another embodiment, microdomains of an acidic resin and microdomains of a basic resin are homogeneously dispersed throughout a matrix resin.

An acidic water-absorbing resin present in a multicomponent SAP particle can be either a strong or a weak acidic water-absorbing resin. The identity of the acidic water-absorbing resin is not limited as long as the resin is capable of swelling and absorbing at least ten times its weight in water, when in a neutralized form. The acidic resin is present in its acidic form, i.e., about 75% to 100% of the acidic moieties are present in the free acid form. As illustrated hereafter, although the free acid form of a acidic water-absorbing resin is generally a poor water absorbent, the combination of an acidic resin and a basic resin in a present multicomponent SAP particle provides excellent water absorption and retention properties.

The acidic water-absorbing resin typically is a lightly crosslinked acrylic-type resin, like lightly crosslinked polyacrylic acid. The lightly crosslinked acidic resin typically is prepared by polymerizing an acidic monomer containing an acyl moiety, e.g., acrylic acid, or a moiety capable of providing an acid group, i.e., acrylonitrile, in the presence of a crosslinker, i.e., a polyfunctional organic compound. The acidic resin can contain other copolymerizable units, i.e., other monoethylenically unsaturated comonomers, well known in the art, as long as the polymer is substantially, i.e., at least 10%, and preferably at least 25%, acidic monomer units. To achieve the full advantage of the present invention, the acidic resin contains at least 50%, and more preferably, at least 75%, and up to 100%, acidic monomer units. The other copolymerizable units can, for example, help improve the hydrophilicity of the polymer.

As set forth above, polymerization of acidic monomers most commonly is performed by free radical processes in the presence of a polyfunctional organic compound. The acidic resins are crosslinked to a sufficient extent such that the polymer is water insoluble. Crosslinking renders the acidic resins substantially water insoluble, and, in part, serves to determine the absorption capacity of the resins. For use in absorption applications, an acidic resin is lightly crosslinked, i.e., has a crosslinking density of less than about 20%, preferably less than about 10%, and most preferably about 0.01% to about 7%.

A crosslinking agent most preferably is used in an amount of less than about 7 wt %, and typically about 0.1 wt % to about 5 wt %, based on the total weight of monomers. Examples of crosslinking polyvinyl monomers include, but are not limited to, polyacrylic (or polymethacrylic) acid esters represented by the following formula (III); and bisacrylamides, represented by the following formula (IV).

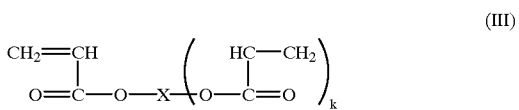

wherein x is ethylene, propylene, trimethylene, hexamethylene, 2-hydroxypropylene, $-(CH_2CH_2O)_nCH_2CH_2-$, or

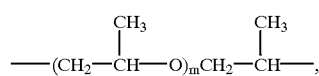

n and m are each an integer 5 to 40, and k is 1 or 2;

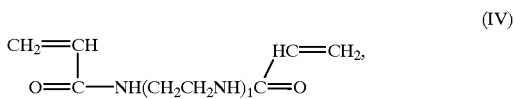

wherein 1 is 2 or 3.

The compounds of formula (III) are prepared by reacting polyols, such as ethylene glycol, propylene glycol, trimethylolpropane, 1,6-hexanediol, glycerin, pentaerythritol, polyethylene glycol, or polypropylene glycol, with acrylic acid or methacrylic acid. The compounds of formula (IV) are obtained by reacting polyalkylene polyamines, such as diethylenetriamine and triethylenetetramine, with acrylic acid.

Specific crosslinking monomers include, but are not limited to, 1,4-butanediol diacrylate, 1,4-butanediol dimethacrylate, 1,3-butylene glycol diacrylate, 1,3-butylene glycol dimethacrylate, diethylene glycol diacrylate, diethylene glycol dimethacrylate, ethoxylated bisphenol A diacrylate, ethoxylated bisphenol A dimethacrylate, ethylene glycol dimethacrylate, 1,6-hexanediol diacrylate, 1,6-hexanediol dimethacrylate, neopentyl glycol dimethacrylate, polyethylene glycol diacrylate, polyethylene glycol dimethacrylate, triethylene glycol diacrylate, triethylene glycol dimethacrylate, tripropylene glycol diacrylate, tetraethylene glycol diacrylate, tetraethylene glycol dimethacrylate, dipentaerythritol pentaacrylate, pentaerythritol tetraacrylate, pentaerythritol triacylate, trimethylolpropane triacrylate, trimethylolpropane trimethacrylate, tris(2-hydroxyethyl)isocyanurate triacrylate, tris(2-hydroxyethyl)isocyanurate trimethacrylate, divinyl esters of a polycarboxylic acid, diallyl esters of a polycarboxylic acid, triallyl terephthalate, diallyl maleate, diallyl fumarate, hexamethylenebismaleimide, trivinyl trimellitate, divinyl adipate, diallyl succinate, a divinyl ether of ethylene glycol, cyclopentadiene diacrylate, or mixtures thereof. Compounds like divinylbenzene and divinyl ether also can be used to crosslink the poly(dialkylaminoalkyl acrylamides).

Especially preferred crosslinking agents are N,N'-methylenebisacrylamide, N,N'-methylenebismethacrylamide, ethylene glycol dimethacrylate, and trimethylolpropane triacrylate.

The acidic resin, either strongly acidic or weakly acidic, can be any resin that acts as an SAP in its neutralized form. The acidic resins typically contain a plurality of carboxylic acid, sulfonic acid, phosphonic acid, phosphoric acid, and/or sulfuric acid moieties. Examples of acidic resins include, but are not limited to, polyacrylic acid, hydrolyzed starch-acrylonitrile graft copolymers, starch-acrylic acid graft copolymers, saponified vinyl acetate-acrylic ester copolymers, hydrolyzed acrylonitrile copolymers, hydrolyzed acrylamide copolymers, ethylene-maleic anhydride copolymers, isobutylene-maleic anhydride copolymers, poly(vinylsulfonic acid), poly(vinylphosphonic acid), poly(vinylphosphoric acid), poly(vinylsulfuric acid), sulfonated polystyrene, and mixtures thereof. The preferred acidic resins are the polyacrylic acids.

The multicomponent SAPs can contain individual microdomains that: (a) contain a single acidic resin or (b) contain more than one, i.e., a mixture, of acidic resins. The multicomponent SAPs also can contain microdomains wherein a portion of the microdomains contain a first acidic resin or acidic resin mixture, and the remaining portion contains a second acid resin or acidic resin mixture.

Analogous to the acidic resin, the basic water-absorbing resin present in the present SAP particles can be a strong or weak basic water-absorbing resin. The identity of the basic resin is not limited as long as the basic resin is capable of swelling and absorbing at least 10 times its weight in water, when in a charged form. The weak basic resin typically is present in its free base, or neutral, form, i.e., about 75% to about 100% of the basic moieties, e.g., amino groups, are present in a neutral, uncharged form. The strong basic resins typically are present in the hydroxide (OH) form.

The basic water-absorbing resin typically is a lightly crosslinked acrylic type resin, like a poly(vinylamine) or a poly(dialkylaminoalkyl (meth)acrylamide). he basic resin also can be a polymer such as a lightly crosslinked polyethylenimine, a poly(vinylguanidine), a poly(dimethyldiallylammonium hydroxide), a quaternized polystyrene derivative, like

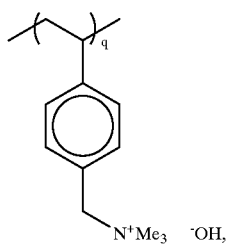

a guanidine-modified polystyrene, like

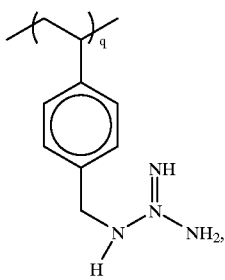

a quaternized poly((meth)acrylamide) or ester analog, like

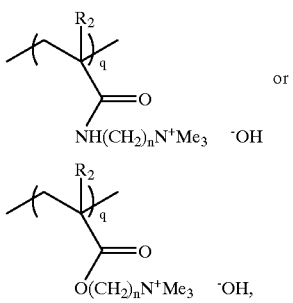

wherein Me is methyl, $R_2$ is hydrogen or methyl, n is a number 1 to 8, and q is a number from 10 to about 10,000, or a poly(vinylguanidine), i.e., poly(VG), a strong basic water-absorbing resin having the general structural formula (V)

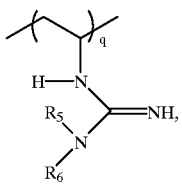

(V)

wherein q is a number from 10 to about 10,000, and $R_5$ and $R_6$, independently, are selected from the group consisting of hydrogen, $C_1$–$C_4$ alkyl, $C_3$–$C_6$ cycloalkyl, benzyl, phenyl, alkyl-substituted phenyl, naphthyl, and similar aliphatic acid aromatic groups. The lightly crosslinked basic water-absorbing resin can contain other polymerizable units and is crosslinked using a polyfunctional organic compound, as set forth above with respect to the acidic water-absorbing resin.

A basic water-absorbing resin used in the present SAP particles typically contains an amino or a guanidino group. Accordingly, a water-soluble basic resin also can be crosslinked in solution by suspending or dissolving an uncrosslinked basic resin in an aqueous or alcoholic medium, then adding a di- or polyfunctional compound capable of crosslinking the basic resin by reaction with the amino groups of the basic resin. Such crosslinking agents include, for example, multifunctional aldehydes (e.g., glutaraldehyde), multifunctional acrylates (e.g., butanediol diacrylate, TMPTA), halohydrins (e.g., epichlorohydrin), dihalides (e.g., dibromopropane), disulfonate esters (e.g., $ZA(O_2)O-(CH_2)_n-OS(O)_2Z$, wherein n is 1 to 10, and Z is methyl or tosyl), multifunctional epoxies (e.g., ethylene glycol diglycidyl ether), multifunctional esters (e.g., dimethyl adipate), multifunctional acid halides (e.g., oxalyl chloride), multifunctional carboxylic acids (e.g., succinic acid), carboxylic acid anhydrides (e.g., succinic anhydride), organic titanates (e.g., TYZOR AA from DuPont), melamine resins (e.g., CYMEL 301, CYMEL 303, CYMEL 370, and CYMEL 373 from Cytec Industries, Wayne, N.J.), hydroxymethyl ureas (e.g., N,N'-dihydroxymethyl-4,5-dihydroxyethyleneurea), and multifunctional isocyanates (e.g., toluene diisocyanate). Crosslinking agents also are disclosed in Pinschmidt, Jr. et al. U.S. Pat. No. 5,085,787, incorporated herein by reference, and in EP 450 923.

In general, the crosslinking agent should be water or alcohol soluble and possess sufficient reactivity with the basic resin such that crosslinking occurs in a controlled fashion, preferably at a temperature of about 25° C. to about 150° C. Preferred crosslinking agents are ethylene glycol diglycidyl ether (EGDGE), a water-soluble diglycidyl ether, and a dibromoalkane, an alcohol-soluble compound.

The basic resin, either strongly or weakly basic, therefore, can be any resin that acts as an SAP in its charged form. The basic resin typically contains amino or guanidino moieties. Examples of basic resins include a poly(vinylamine), a polyethylenimine, a poly(vinylguanidine), or a poly(dialkylaminoalkyl (meth)acrylamide) prepared by polymerizing and lightly crosslinking a monomer having the structure

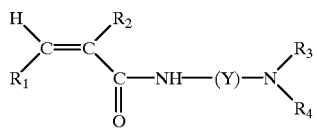

or its ester analog

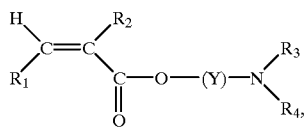

wherein $R_1$ and $R_2$, independently, are selected from the group consisting of hydrogen and methyl, Y is a divalent straight chain or branched organic radical having 1 to 8 carbon atoms, and $R_3$ and $R_4$, independently, are alkyl radicals having 1 to 4 carbon atoms.

Preferred basic resins include a poly(vinylamine), polyethylenimine, poly (vinylguanadine), poly (dimethylaminoethyl acrylamide) (poly(DAEA)), and poly (dimethylaminopropyl methacrylamide) (poly (DMAPMA)).

Analogous to microdomains containing an acidic resin, the present multicomponent SAPs can contain microdomains of a single basic resin, microdomains containing a mixture of basic resins, or microdomains of different basic resins.

The present multicomponent SAPs can be prepared by various methods. It should be understood that the exact method of preparing a multicomponent SAP is not limited by the following embodiments. Any method that provides a particle having microdomains of an acidic and/or basic resin in intimate contact with each other or a continuous phase of an acidic resin, basic resin, and/or matrix resin is suitable.

In one method, dry particles of a basic resin, optionally surface crosslinked, are admixed into a rubbery gel of an acidic resin. The resulting mixture is extruded, then dried, and optionally surface crosslinked, to provide multicomponent SAP particles having microdomains of a basic resin homogeneously dispersed throughout a continuous phase of an acidic resin. Alternatively, particles of an acidic resin, optionally surface crosslinked, can be admixed into a rubbery gel of a basic resin, and the resulting mixture is extruded and dried, and optionally surface crosslinked, to provide multicomponent SAP particles having microdomains of an acidic resin homogeneously dispersed throughout a continuous phase of a basic resin. The method also can be employed using dry particles of an acidic resin and a gel of a basic resin.

In another method, dry particles of an acidic resin can be admixed with dry particles of a basic resin, and the resulting mixture is formed into a hydrogel, then extruded, to form multicomponent SAP particles.

In yet another method, a rubbery gel of an acidic resin and a rubbery gel of a basic resin, each optionally surface crosslinked, are coextruded, and the coextruded product is dried, and optionally surface crosslinked, to form multicomponent SAP particles containing microdomains of the acidic resin and the basic resin dispersed throughout the particle.

The method of preparing the present multicomponent SAP particles, therefore, is not limited, and does not require an extrusion step. Persons skilled in the art are aware of other methods wherein the multicomponent SAP contains microdomains of an acidic resin and/or a basic resin cure in intimate contact with each other, with a matrix resin, or with an acidic and/or basic resin. One example is agglomeration of an acidic and/or basic resin with each other or another acidic and/or basic resin to provide a multicomponent SAP particle containing microdomains of an acidic and/or basic resin.

In embodiments wherein an acidic resin and a basic resin are present as microdomains within a matrix of a matrix resin, particles of an acidic resin and a basic resin are admixed with a rubbery gel of a matrix resin, and the resulting mixture is extruded, then dried, to form multicomponent SAP particles having microdomains of an acidic resin and a basic resin dispersed in a continuous phase of a matrix resin. Alternatively, rubbery gels of an acidic resin, basic resin, and matrix resin can be coextruded to provide a multicomponent SAP containing microdomains of an acidic resin, a basic resin, and a matrix resin dispersed throughout the particle. In this embodiment, the acidic resin, basic resin, and resulting multicomponent SAP, each can be optionally surface crosslinked.

The matrix resin is any resin that allows fluid transport such that a liquid medium can contact the acidic and/or basic resin. The matrix resin typically is a hydrophilic resin capable of absorbing water. Nonlimiting examples of matrix resins include poly(vinyl alcohol), poly(N-vinylformamide), polyethylene oxide, poly(meth)acrylamide, poly (hydroxyethyl acrylate), hydroxyethylcellulose, methylcellulose, and mixtures thereof. The matrix resin also can be a conventional water-absorbing resin, for example, a polyacrylic acid neutralized greater than 25 mole %, and typically greater than 50 mole %.

In preferred embodiments, the acidic resin, the basic resin, and/or the multicomponent SAP particles are surface crosslinked. In especially preferred embodiments, the acidic and/or basic resins comprising the multicomponent SAP particles are surface crosslinked, and the entire multicomponent SAP particle is surface crosslinked. It has been found that surface crosslinking of an acidic resin, a basic resin, and/or a multicomponent SAP particle of the present invention enhances the ability of the resin or multicomponent SAP particle to absorb and retain aqueous media under a load.

Surface crosslinking is achieved by spraying an acidic resin, a basic resin, and/or a multicomponent SAP particle with a solution of a surface cross-linking agent to wet predominantly only the outer surfaces of the resin or SAP particle. Surface crosslinking and drying of the resin or SAP particle then is performed, preferably by heating at least the wetted surfaces of the resin or SAP particles.

Typically, the resins and/or SAP particles are surface treated with an aqueous or an alcoholic solution of a surface crosslinking agent. The solution contains about 0.01% to about 4%, by weight, surface crosslinking agent, and preferably about 0.4% to about 2%, by weight, surface crosslinking agent in a suitable solvent. The solution can be applied as a fine spray onto the surface of freely tumbling resin particles or multicomponent SAP particles at a ratio of about 1:0.01 to about 1:0.5 parts by weight resin or SAP particles to solution of surface crosslinking agent. The surface crosslinker is present in an amount of 0% to about 1%, by weight of the resin or SAP particle, and preferably 0% to about 0.5% by weight. To achieve the full advantage of the present invention, the surface crosslinker is present in an amount of about 0.001% to about 0.1% by weight.

The crosslinking reaction and drying of the surface-treated resin or multicomponent SAP particles are achieved by heating the surface-treated polymer at a suitable temperature, e.g., about 25° C. to about 150° C., and preferably about 105° C. to about 120° C. However, any other method of reacting the crosslinking agent to achieve surface crosslinking of the resin or multicomponent SAP particles, and any other method of drying the resin or multicomponent SAP particles, such as microwave energy, or the like, can be used.

With respect to the basic resin, or multicomponent SAP particles having a basic resin present on the exterior surface of the particles, suitable surface crosslinking agents include di- or polyfunctional molecules capable of reacting with amino groups and crosslinking a basic resin. Preferably, the surface crosslinking agent is alcohol or water soluble and possesses sufficient reactivity with a basic resin such that crosslinking occurs in a controlled fashion at a temperature of about 25° C. to about 150° C.

Nonlimiting examples of suitable surface crosslinking agents for basic resins include:

(a) dihalides and disulfonate esters, for example, compounds of the formula

Y—(CH$_2$)$_p$—Y, wherein p is a number from 2 to 12, and Y, independently, is halo (preferably bromo), tosylate, mesylate, or other alkyl or aryl sulfonate esters;

(b) multifunctional aziridines;

(c) multifunctional aldehydes, for example, glutaraldehyde, trioxane, paraformaldehyde, terephthaldehyde, malonaldehyde, and glyoxal, and acetals and bisulfites thereof;

(d) halohydrins, like epichlorohydrin;

(e) multifunctional epoxy compounds, for example, ethylene glycol diglycidyl ether, bisphenol A diglycidyl ether, and bisphenol F diglycidyl ether, (f) multifunctional carboxylic acids and esters, acid chlorides, and anhydrides derived therefrom, for example, di- and polycarboxylic acids containing 2 to 12 carbon atoms, and the methyl and ethyl esters, acid chlorides, and anhydrides derived therefrom, like oxalic acid, adipic acid, succinic acid, dodecanoic acid, malonic acid, and glutaric acid, and esters, anhydrides, and acid chlorides derived therefrom;

(g) organic titanates, like TYZOR AA, available from E.I. DuPont de Nemours, Wilmington, Del.;

(h) melamine resins, like the CYMEL resins available from Cytec Industries, Wayne, N.J.;

(i) hydroxymethyl ureas, like N,N'-dihydroxymethyl-4,5-dihydroxyethylene urea;

(j) multifunctional isocyanates, like toluene diisocyanate, isophorone diisocyanate, xylene diisocyanate, and hexamethylene diisocyanate; and (k) other crosslinking agents for basic water-absorbing resins known to persons skilled in the art.

A preferred surface crosslinking agent is a dihaloalkane, ethylene glycol diglycidyl ether (EGDGE), or a mixture thereof, which crosslink a basic resin at a temperature of about 25° C. to about 150° C. Especially preferred surface crosslinking agents are dibromoalkanes containing 3 to 10 carbon atoms and EGDGE.

With respect to the acidic water-absorbing resins, or multicomponent SAP particles having an acidic resin on the exterior surface of the particles, suitable surface crosslinking agents are capable of reacting with acid moieties and crosslinking the acidic resin. Preferably, the surface crosslinking agent is alcohol soluble or water soluble, and possesses sufficient reactivity with an acidic resin such that crosslinking occurs in a controlled fashion, preferably at a temperature of about 25° C. to about 150° C.

Nonlimiting examples of suitable surface crosslinking agents for acidic resins include:

(a) polyhydroxy compounds, like glycols and glycerol;

(b) metal salts;

(c) quaternary ammonium compounds;

(d) a multifunctional epoxy compound;

(e) an alkylene carbonate, like ethylene carbonate or propylene carbonate;

(f) a polyaziridine, like 2,2-bishydroxymethyl butanol tris[3-(1-aziridine propionate]);

(g) a haloepoxy, like epichlorhydrin;

(h) a polyamine, like ethylenediamine;

(i) a polyisocyanate, like 2,4-toluene diisocyanate; and (j) other crosslinking agents for acidic water-absorbing resins known to persons skilled in the art.

In accordance with an important feature of the present invention, either the acidic resin or the basic resin can be the continuous phase of a present multicomponent SAP particle. Likewise, either the acidic resin or the basic resin can be the dispersed microdomain phase. In addition, a strong acidic resin can be used with either a strong basic resin or a weak basic resin. A weak acidic resin can be used with a strong basic resin or a weak basic resin. Preferably, the acidic resin is a weak acidic resin and the basic resin is a weak basic resin. In preferred embodiments, the weak acidic resin, the weak basic resin, and/or the multicomponent SAP particles are surface crosslinked.

As previously discussed, sodium poly(acrylate) is considered the best SAP, and, therefore, is the most widely used SAP in commercial applications. Sodium poly(acrylate) has polyelectrolytic properties that are responsible for its superior performance in absorbent applications. These properties include a high charge density, and charge relatively close to the polymer backbone.

However, an acidic resin in the free acid form, or a basic resin in the free base form, typically do not function as an SAP because there is no ionic charge on either type of polymer. A poly(acrylic acid) resin, or a poly(vinylamine) resin, are neutral polymers, and, accordingly, do not possess the polyelectrolytic properties necessary to provide an SAP. The driving force for water absorption and retention, therefore, is lacking. This is illustrated in Tables 1 and 2 showing the relatively poor absorption and retention properties for a neutral poly(DAEA) in absorbing synthetic urine. However, when converted to a salt, an acidic resin, like a polyacrylic acid, or a basic resin, like a poly (dialkylaminoalkyl (meth)acrylamide), then behave like an SAP.

It has been found that basic resins, in their free base form, are useful components in superabsorbent materials further containing an acidic water-absorbing resin. For example, a superabsorbent material comprising an admixture of a poly (dialkylaminoalkyl (meth)acrylamide) and an acidic water-absorbing resin, like polyacrylic acid, demonstrates good water absorption and retention properties. Such an SAP material comprises two uncharged, slightly crosslinked polymers, each of which is capable of swelling and absorbing aqueous media. When contacted with water or an aqueous electrolyte-containing medium, the two uncharged polymers neutralize each other to form a superabsorbent material. This also reduces the electrolyte content of the medium absorbed by polymer, further enhancing the polyelectrolyte effect. Neither polymer in its uncharged form behaves as an SAP by itself when contacted with water. However, superabsorbent materials, which contain a simple mixture of two resins, one acidic and one basic, are capable of acting as an absorbent material because the two resins are converted to their polyelectrolyte form. These superabsorbent materials have demonstrated good water absorption and retention properties. However, the present multicomponent SAP particles, containing microdomains of an acidic resin and/or a basic resin, exhibit improved water absorption and retention over simple mixtures of acidic resin particles and basic resin particles.

In the present multicomponent SAP particles, the weak basic resin is present in its free base, e.g., amine, form, and the acidic resin is present in its free acid form. It is envisioned that a low percentage, i.e., about 25% or less, of the amine and/or acid functionalities can be in their charged form. The low percentage of charged functionalities does not adversely affect performance of the SAP particles, and can assist in the initial absorption of a liquid. A strong basic resin is present in the hydroxide, or charged, form.

The present multicomponent SAP particles are useful in articles designed to absorb large amounts of liquids, especially electrolyte-containing liquids, such as in diapers and catamenial devices.

The following examples illustrate the preparation of the multicomponent SAP particles of the present invention.

EXAMPLE 1

Preparation of Poly(acrylic acid) 0% Neutralized (Poly(AA) DN-0)

A monomer mixture containing acrylic acid (270 grams), deionized water (810 grams), methylenebisacrylamide (0.4 grams), sodium persulfate (0.547 grams), and 2-hydroxy-2-methyl-1-phenyl-propan-1-one (0.157 grams) was prepared, then sparged with nitrogen for 15 minutes. The monomer mixture was placed into a shallow glass dish, then the monomer mixture was polymerized under 15 mW/cm$^2$ of UV light for 25 minutes. The resulting poly(AA) was a rubbery gel.

The rubbery poly(AA) gel was cut into small pieces, then extruded through a KitchenAid Model K5SS mixer with meat grinder attachment. The extruded gel was dried in a forced-air oven at 120°0 C., and finally ground and sized through sieves to obtain the desired particle size.

This procedure provided a polyacrylic acid hydrogel with a degree of neutralization of zero (DN=0).

EXAMPLE 2

Preparation of Poly(dimethylaminoethyl acrylamide) (Poly (DAEA))

A monomer mixture containing 125 grams N-(2-dimethylaminoethyl) acrylamide (DAEA), 300 grams deionized water, 0.6 gram methylenebisacrylamide, and 0.11 grams V-50 initiator (i.e., 2,2'-azobis(2-amidinopropane) hydrochloride initiator available from Wako Pure Chemical Industries, Inc., Osaka, Japan) was sparged with argon for 15 minutes. Then the resulting reaction mixture was placed in a shallow dish and polymerized under 15 mW/cm$^2$ of UV light for 25 minutes. The polymerization was exothermic, eventually reaching about 100° C. The resulting poly (DAEA) was a rubbery gel. The rubbery poly(DAEA) gel was crumbled by hand, then dried at 60° C. for 16 hours, and finally ground and sized through sieves to obtain the desired particle size.

EXAMPLE 3

Preparation of Poly (dimethylaminopropyl methacrylamide) (Poly(DMAPMA))

A monomer mixture containing DMAPMA monomer (100 grams), deionized water (150 grams), methylenebisacrylamide (0.76 grams) and V-50 initiator (0.72 grams) was placed in a glass beaker. The monomer mixture was purged with argon for 25 minutes, covered, and then placed in an oven at about 60° C. for about 60 hours. The resulting poly(DMAPMA) was a rubbery gel. The rubbery poly (DMAPMA) gel was crumbled by hand, dried at 60° C. for 16 hours, and then ground and sized through sieves to obtain the desired particle size.

EXAMPLE 4

Preparation of a Poly(N-vixnylformamide) and a Poly(vinylamine)

A monomer mixture containing N-vinylformamide (250 grams), deionized water (250 grams), methylenebisacrylamide (1.09 grams), and V-50 initiator (0.42 grams) was placed in a shallow dish, then polymerized under an ultraviolet lamp as set forth in Example 1 until the mixture polymerized into a rubbery gel. The poly(N-vinylformamide) then was hydrolyzed with a sodium hydroxide solution to yield a lightly crosslinked poly (vinylamine).

EXAMPLE 5

Preparation of a Strong Acidic Water-Absorbing Resin

A monomer mixture containing acrylic acid (51 grams), 2-acrylamido-2-methyl-1-propanesulfonic acid (AMPS, 25.8 grams), deionized water (230 grams), methylenebisacrylamide (0.088 grams), sodium persulfate (0.12 grams), and 2-hydroxy-2-methyl-1-phenyl-propan-1-one (0.034 grams) was prepared, then placed in shallow dish and polymerized under an ultraviolet lamp as set forth in Example 1 until the monomer mixture polymerizes into rubbery gel.

The gel was cut into small pieces then extruded through a KitchenAid Model K5SS mixer with a meat grinder attachment. The extruded gel then was dried in a forced-air oven at 120° C., ground, and sized through sieves to obtain the desired particle size.

This resulting acidic resin contained 15 mole percent strong acid functionality (—$SO_3H$) and 85 mole percent weak acid functionality (—$CO_2H$).

EXAMPLE 6

Preparation of a Crosslinked Poly(vinyl alcohol-co-vinylamine) Resin

Poly(vinyl alcohol-co-vinylamine) (50 grams, 6 mol % vinylamine), available from Air Products Inc., Allentown, Pa., was dissolved in 450 grams of deionized water in a glass jar to form a viscous solution. Ethylene glycol diglycidyl ether (0.2 grams) was added to the viscous solution, with stirring. The jar then was covered and placed in a 60° C. oven for 16 hours to yield a rubbery gel of a lightly crosslinked poly(vinyl alcohol-co-vinylamine).

EXAMPLE 7

Preparation of a Crosslinked Poly(vinylamine) Resin

To 2 liters of a 3% by weight aqueous poly(vinylamine) solution was added 0.18 g of ethyleneglycol diglycidyl ether (EGDGE). The resulting mixture was stirred to dissolve the EGDGE, then the mixture was heated to about 60° C. and held for one hour to gel. The gel was heated to about 80° C. and held until about 90% of the water was removed. The resulting get then was extruded and dried to a constant weight at 80° C. The dried, lightly crosslinked poly(vinylamine) then was cryogenically milled to form a granular material.

EXAMPLE 8

Preparation of a Poly(DAEA)/Poly(kA) Multicomponent SAP (Poly(AA) Continuous Phase)

The undried, rubbery poly(AA) hydrogel prepared in Example 1 (133 grams) was cut into pieces and extruded through a KitchenAid Model K5SS mixer with meat grinder attachment. The gel then was mixed with 50 grams of the dry poly(DAEA) particles (<106 microns in size) prepared in Example 2. The resulting mixture was extruded three times using the KitchenAid mixer, then dried in a 60° C. forced-air oven for 16 hours and finally ground and sized through sieves to obtain the desired particle size. The process yielded 83 grams of multicomponent SAP particles comprising poly(DAEA) microdomains dispersed in a continuous poly(AA) phase, and having a weight ratio of poly(DAEA) to poly(AA) of about 60/40.

EXAMPLE 9

Surface Treatment of the Poly(DAEA)/Poly(AA) Multicomponent SAP of Example 8

A surface-treating solution was prepared by admixing 0.15 grams EGDGE, 7.88 grams propylene glycol, and 1.97 grams deionized water until homogeneous. Ten grams of the poly(DAEA)/poly(AA) multicomponent SAP of Example 8 were placed in a beaker fitted with a vertical shaft stirrer. The dry multicomponent SAP was stirred at a sufficient speed to fluidize the SAP in the beaker, then 0.4 grams of the surface-treating solution was added to the fluidized SAP dropwise via syringe. Then, stirring was stopped, and the beaker was placed in a 125° C. forced-air oven for one hour to yield a poly(DAEA)/poly(AA) multicomponent SAP surface treated with 600 ppm of EGDGE.

EXAMPLE 10

Preparation of a Poly(AA)/Poly(DMAPM) Multicomponent SAP (Poly(DMAPMA) Continuous Phase)

The poly(DMAPMA) hydrogel prepared in Example 3 (70 grams) was cut into pieces and extruded through a KitchenAid Model K5SS mixer with meat grinder attachment. The gel then was mixed with 32 grams of dry poly(AA) particles (<106 microns in size) prepared in Example 1. The resulting mixture then was extruded three times using the KitchenAid mixer, followed by drying in a 60° C. forced-air oven at 60° C. for 16 hours, and finally grinding and sizing through sieves to obtain the desired particle size. The process yielded 60 grams of multicomponent SAP particles comprising poly(AA) microdomains dispersed in a continuous poly(DMAPMA) phase, and having a poly(AA) to poly(DMAPMA) weight ratio of about 50/50.

EXAMPLE 11

Surface Treatment of the Poly(AA)/Poly (DMAPMA) Multicomponent SAP of Example 10

A surface-treating solution was prepared by admixing 0.375 grams 1,8-dibromooctane and 9.625 grams isopropanol until homogeneous. Ten grams of the poly(AA)/poly (DMAPMA) multicomponent SAP of Example 10 were placed in a beaker fitted with a vertical shaft stirrer. The dry multicomponent SAP was stirred at a sufficient speed to fluidize the SAP in the beaker, then 0.4 grams of the surface-treating solution was added to the fluidized SAP dropwise via syringe. Next, stirring was stopped, and the beaker was placed in a 105° C. forced-air oven for one hour to yield a poly(AA)/poly(DMAPMA) multicomponent SAP surface treated with 1,500 ppm of 1,8-dibromooctane.

EXAMPLE 12

Poly(DAEA)/Poly(AA) Multicomponent SAP Prepared by Gel Coextrusion

Thirty grams of the poly(DAEA) of Example 2 were extruded through a KitchenAid Model K5SS mixer with meat grinder attachment. Twenty-four grams of the poly (AA) hydrogel of Example 1 also were extruded through a KitchenAid Model K5SS mixer with meat grinder attachment. The two extrudates then were combined via hand mixing, followed by extruding the resulting mixture two times using the meat grinder. The extruded product then was dried for 16 hours at 60° C., milled and sized to 180–710 microns, and finally surface treated with 200 ppm EGDGE (as described in Example 9). The procedure yields multicomponent SAP containing microdomains of poly(DAEA) and poly(AA), and having poly(DAEA)/poly(AA) weight ratio of about 60/40.

EXAMPLE 13

Preparation of Poly(vin-yluanadine) (Poly(VG))

To 500 ml of an aqueous solution of poly(vinylamine) (1.98% solids, 93% hydrolized) was added 38.5 ml of 6M hydrochloric acid and 9.65 g of cyanamide ($H_2NCN$). The resulting solution was heated under reflux for 8 hours. The solution next was diluted to a volume of 3 L (liters) with a 5% sodium hydroxide solution, then ultrafiltered ($M_w$ cut off of 100,000) with 15 L of a 59 sodium hydroxide solution, followed by 15 L of deionized water. The resulting product was concentrated to a 2.6% solids solution, having a pH 11.54. A poly(vinylamine) solution has a pH 10.0. The 2.6% solids solution gave a negative silver nitrate test, and a gravimetric analysis of the polymer, after the addition of HCl, gave the following composition: vinylguanidine 90%, vinylformamide 7%, and vinylamine 3%. Infrared analysis shows a strong absorption at 1651 $cm^{-1}$, which is not present in poly(vinylamine), and corresponds to a C=N stretch.

EXAMPLE 14

Preparation of a Crosslinked Poly(VG) Resin

The 2.6% solids solution of Example 13 was further concentrated to 12.5% solids by distillation. To this 12.5% solids solution was added 1 mole % EGDGE, and the resulting solution then was heated in a 60° C. oven for 5 hours to form a gel of lightly crosslinked poly (vinylguanidine).

EXAMPLE 15

Preparation of a Coextruded Poly(VG)/Poly(AA) Multi-component SAP

The crosslinked poly(VG) hydrogel of Example 14 was coextruded with 1 mole equivalent of the poly(AA) of Example 1 by the method set forth in Example 12. A portion of the coextruded poly(VG)/poly(AA) multicomponent SAP then was surface cross-linked with 200 ppm EGDGE, by the method set forth in Example 9.

EXAMPLE 16

PEI/Poly(AA) Coextruded Multicomponent SAP Prepared by Gel Coextrusion

Aqueous solutions containing 10% and 20% by weight polyethylenimine (PEI, $M_w$ of 60,000, available commercially as EPOMIN P-1000, Aceto Corp., Lake Success, N.Y.) were crosslinked with 1.0 and 1.5 mole % EGDGE by the method set forth in Example 6, i.e., heating for 16 hours at 60° C., to provide rubbery gels. The rubbery PEI gels (37.4 wt. %) were coextruded with the poly(AA) gel of Example 1 (62.6 wt. %) in accordance with the method set forth in Example 12, and the resulting coextruded multi-component SAPs were dried in an oven at 60° C. The dried multicomponent SAPs then were cryogenically milled, and finally sized.

In the test results set forth below, the multicomponent SAP particles of the present invention were tested for absorption under no load (AUNL) and absorption under load at 0.28 psi and 0.7 psi (AUL (0.28 psi) and AUL (0.7 psi)). Absorption under load (AUL) is a measure of the ability of an SAP to absorb fluid under an applied pressure. The AUL was determined by the following method, as disclosed in U.S. Pat. No. 5,149,335, incorporated herein by reference.

An SAP (0.160 g+/−0.001 g) is carefully scattered onto a 140-micron, water-permeable mesh attached to the base of a hollow plexiglass cylinder with an internal diameter of 25 mm. The sample is covered with a 100 g cover plate and the cylinder assembly weighed. This gives an applied pressure of 20 $g/cm^2$ (0.28 psi). Alternatively, the sample can be covered with a 250 g cover plate to give an applied pressure of 51 $g/cm^2$ (0.7 psi). The screened base of the cylinder is placed in a 100 mm petri dish containing 25 milliliters of a test solution (usually 0.9% saline), and the polymer is allowed to absorb for 1 hour (or 3 hours). By reweighing the cylinder assembly, the AUL (at a given pressure) is calculated by dividing the weight of liquid absorbed by the dry weight of polymer before liquid contact.

The following tables contain absorption and retention data for the multicomponent SAP particles of the present invention, for individual polymers present in the multicomponent SAP particles, and for simple admixtures of the dry resins present in the multicomponent SAP particles. The data shows a significant improvement in water absorption and retention for the present multicomponent SAP particles containing microdomains of an acidic and/or basic resin polymers within each particle compared to the individual resins and a simple admixture of the individual resins. The data in Tables 1–6 shows the improved ability of multicomponent SAP particles of the present invention to absorb and retain an aqueous 0.9% saline solution.

TABLE 1

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
| --- | --- | --- | --- | --- | --- | --- |
| Poly(DAEA) alone[1] | 9.6 | 8.1 | 23.9 | 13.5 | 9.3 | 24.2 |
| Polyacrylic Acid alone[2] | 11.9 | 10.8 | 14.3 | 12.0 | 10.8 | 14.3 |
| SAP-1[3] | 11.0 | 10.9 | 45.2 | 14.8 | 14.4 | 48.0 |
| SAP-2[4] | 12.5 | 9.6 | 26.7 | 18.9 | 13.1 | 30.1 |
| SAP-3[5] | 12.4 | 11.3 | 37.3 | 16.5 | 14.7 | 42.3 |
| SAP-4[6] | 20.1 | 17.2 | 28.6 | 24.7 | 20.7 | 34.1 |
| SAP-5[7] | 25.3 | 18.2 | 35.3 | 28.1 | 23 | 38.7 |
| Multicomponent SAP-1[8] | | | | | | |
| 0[9] | 23.7 | 16.3 | 41.6 | 26.9 | 20 | 41.7 |
| 200 | 26.7 | 24.7 | 41.2 | 27.1 | 25.1 | 39.9 |
| 400 | 27.3 | 24.1 | 43.4 | 27.5 | 24.5 | 44.0 |
| 600 | 29.2 | 23.8 | 41.8 | 29.5 | 24.0 | 41.2 |
| 800 | 26.6 | 24.1 | 40.9 | 26.7 | 24.2 | 41.7 |
| 1,000 | 27.5 | 24.3 | 39.9 | 27.8 | 24.2 | 40.7 |

TABLE 1-continued

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Multicomponent SAP-2[10] | | | | | | |
| 0[9] | 26.3 | 15.4 | 40 | 26.9 | 17.3 | 39.4 |
| 400 | 26.5 | 20.5 | 39.3 | 27 | 22.4 | 40.3 |
| 600 | 27 | 18.3 | 40.2 | 27.1 | 20.7 | 40.6 |

[1] particle size--180–710 μm;
[2] 0% neutralization, particle size--180–710 μm, surface crosslinked--600 ppm EGDGE;
[3] mixture of 60% poly(DAEA), particle sizes less than 180 nm, and 40% polyacrylic acid--0% neutralized;
[4] mixture of 60% poly(DAEA), particle sizes less than 180 nm, and 40% polyacrylic acid-0% neutralized, crosslinked with 600 ppm EGDGE;
[5] mixture of 60% poly(DAEA), particle size--180–710 μm, and 40% polyacrylic acid--0% neutralized;
[6] mixture of 60% poly(DAEA), particle size--180–710 μm, and 40% polyacrylic acid--0% neutralized, crosslinked with 600 ppm EGDGE;
[7] mixture of 60% poly(DAEA), particle sizes less than 180 μm, and 40% polyacrylic acid--20% neutralized, particle size 180–710 μm;
[8] multicomponent SAP containing microdomains of poly(DAEA) (<180 μm) as dispersed phase in poly(AA) (DN = 0) continuous phase, poly(DAEA)/poly(AA) weight ratio--60/40;
[9] ppm surface crosslinking with EGDGE; and
[10] multicomponent SAP containing microdomains of poly(DAEA) (<180 μm) as dispersed phase in poly(AA) (DN = 20) continuous phase, poly(DAEA)/poly(AA) weight ratio--60/40.

TABLE 2

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(DMAPMA)[11] | 10.2 | 8.6 | 18 | 11.4 | 10 | 18.3 |
| Poly(DMAPMA)[12] | 9.3 | 5.2 | 17.4 | 11 | 6.9 | 17.8 |
| Polyacrylic acid[13] | 11.9 | 10.8 | 14.3 | 12.0 | 10.8 | 14.3 |
| SAP-6[14] | 14.5 | 10.9 | 18.8 | 17.2 | 14.3 | 20.9 |
| SAP-7[15] | 14 | 12 | 38.7 | 17.9 | 15.7 | 43.6 |
| SAP-8[16] | 12.5 | 10.4 | 24.8 | 14.5 | 12.4 | 24.8 |
| Multicomponent SAP-3[17] | | | | | | |
| 0[9] | 28.8 | 15 | 41.6 | 31 | 17.5 | 41.5 |
| 100 | 27.4 | 24.2 | 38.8 | 27.1 | 23.6 | 38.8 |
| 200 | 27.3 | 24.2 | 39.8 | 25.8 | 23 | 39 |
| 400 | 26 | 23 | 37 | 25.2 | 22.5 | 36.4 |
| 600 | 25.1 | 22.3 | 37.1 | 24.7 | 21.3 | 36.1 |
| Multicomponent SAP-4[18] | | | | | | |
| 0[9] | 31.9 | 11.6 | 44.2 | 31.8 | 15.7 | 44.9 |
| 200 | 27.6 | 24.3 | 37.8 | 27.5 | 23.4 | 38.1 |
| 400 | 27.5 | 23.7 | 37.4 | 27.2 | 23.1 | 38.8 |
| Multicomponent SAP-5[19] | | | | | | |
| 0[20] | 23.6 | 12.9 | 37.9 | 25 | 14.4 | 38.5 |
| 1500 | 24.7 | 16.9 | 36.4 | 25.5 | 18.3 | 37.5 |

[11] Poly(DMAPMA), particle size less than 106 μm;
[12] Poly(DMAPMA), particle size 106–180 μm;
[13] Polyacrylic acid, particle size 180–710 μm--0% neutralized, surface crosslinked with 600 ppm EGDGE;
[14] mixture of 60% Poly(DMAPMA), particle size 106–180 μm, and 40% polyacrylic acid--0% neutralized;
[15] mixture of 60% Poly(DMAPMA), particle size <106 μm, and 40% polyacrylic acid--0% neutralized;
[16] mixture of 50% Poly(DMAPMA), and 50% polyacrylic acid--0% neutralized;
[17] multicomponent SAP containing microdomains of poly(DMAPMA) (<106 μm) as dispersed phase in poly(AA) (DN = 0) continuous phase, poly(DMAPMA)/poly(AA) weight ratio 60/40;
[18] multicomponent SAP containing microdomains of poly(DMAPMA) (106–180 μm) as dispersed phase in poly(AA) (DN = 0) continuous phase, poly(DMAPMA)/poly(AA) weight ratio 60/40;
[19] multicomponent SAP containing microdomains of poly(AA) (DN = 0%) (<106 μm) as dispersed phase in poly(DMAPMA) continuous phase, poly(AA)/poly(DMAPMA) weight ratio 50/50; and
[20] ppm surface crosslinking with dibromooctane.

TABLE 3

| SAP | AUL (0.28 psi, 1 hr.) | AUL (0.7 psi, h4.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylamine) alone | 14.2 | 14.4 | 21.4 | 15 | 14.3 | 23.4 |
| SAP-9[21] | 21.2 | 18.6 | 28.3 | 23.8 | 20.5 | 36.3 |
| Multicomponent SAP-6[22] | | | | | | |
| 0[9] | 14.9 | 12.8 | 53.8 | 16.9 | 15.6 | 55.4 |
| 100 | 37.5 | 30.1 | 45.5 | 37.5 | 30.1 | 45.5 |
| 200 | 36.2 | 30.4 | 48.5 | 35.9 | 30.2 | 47.4 |
| 400 | 34.6 | 30.6 | 44.9 | 34.6 | 30.6 | 46.2 |

[21]mixture of 37% poly(vinylamine) and 63% poly(AA); and
[22]multicomponent SAP containing microdomains of poly(vinylamine) (<180 μm) as dispersed phase in poly(AA) (DN = 0) continuous phase, poly(vinylamine)/poly(AA) weight ratio--37/63.

TABLE 4

Coextruded Multicomponent SAP of Example 12
(60/40 weight ratio poly(DAEA)/poly(AA))

| Surface Treatment | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| 0 | 30.5 | 13.3 | 41.1 | 30.6 | 16.3 | 40.2 |
| 200 ppm EGDGE | 31 | 27.7 | 40.2 | 30.8 | 27.3 | 39.9 |

TABLE 5

| SAP | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|
| Poly(vinylguanidine) hydrochloride alone | 21 | 16.1 | 31.2 | 22.4 | 18.0 | 32.7 |
| Multicomponent SAP-7[23] | | | | | | |
| 0[9] | 18.8 | 12.7 | 40.6 | 21.2 | 15.3 | 46.8 |
| 200 | 22 | 19.2 | 33.5 | 23.5 | 20.3 | 37.4 |

[23]multicomponent SAP containing microdomains of poly(VG) and poly(AA), with a poly(VG)/poly(AA) weight ratio--50/50.

TABLE 6

Coextruded Multicomponent SAP of Example 16
(37.4/62.6 weight ratio PEI/poly(AA))

| PEI Gel (% Solids) | Crosslinker Level[24] | AUL (0.28 psi, 1 hr.) | AUL (0.7 psi, 1 hr.) | AUNL (1 hr.) | AUL (0.28 psi, 3 hr.) | AUL (0.7 psi, 3 hr.) | AUNL (3 hr.) |
|---|---|---|---|---|---|---|---|
| 20 | 1.0 | 23 | 19.5 | 32 | 24.3 | 20.8 | 34.9 |
| 10 | 1.5 | 20.1 | 16.2 | 28.4 | 22.4 | 18.1 | 31.9 |

[24]mole % EGDGE.

Many modifications and variations of the invention as hereinbefore set forth can be made without departing from the spirit and scope thereof and, therefore, only such limitations should be imposed as are indicated by the appended claims.

What is claimed is:

1. A multicomponent superabsorbent particle comprising microdomains of at least one basic water-absorbing resin dispersed throughout a continuous phase of at least one acidic water-absorbing resin, said particle having a weight ratio of acidic resin to basic resin of about 90:10 to about 10:90, wherein the acidic resin has about 75% to 100% acid moieties present in the free acid form, and the basic resin has about 75% to 100% basic moieties present in a free base form.

2. The particle of claim 1 wherein the basic resin comprises a strong basic resin, and the acidic resin comprises a strong acidic resin, a weak acidic resin, or a mixture thereof.

3. The particle of claim 1 wherein the basic resin comprises a weak basic resin, and the acidic resin comprises a strong acidic resin, a weak acidic resin, or a mixture thereof.

4. The particle of claim 1 containing about 50% to 100%, by weight, of basic resin plus acidic resin.

5. The particle of claim 1 wherein the particle is about 10 to about 10,000 microns in diameter.

6. The particle of claim 1 wherein the basic resin is surface crosslinked with up to about 1% by weight of the particle of a surface crosslinking agent.

7. The particle of claim 6 wherein the surface crosslinking agent is selected from the group consisting of (a) a dihalide or a disulfonate ester having the formula

wherein p is an integer 2 to 12 and Y, independently, is halo, tosylate, mesylate, an alkyl sulfonate ester, or an aryl sulfonate ester;

(b) a multifunctional aziridine;

(c) a multifunctional aldehyde, and acetals and bisulfites thereof;

(d) a halohydrin;

(e) a multifunctional epoxy compound;

(f) a multifunctional carboxylic acid containing 2 to 12 carbon atoms, and methyl and ethyl esters, acid chlorides, and anhydrides derived therefrom;

(g) an organic titanate;

(h) a melamine resin;

(i) a hydroxymethyl urea; and (j) a multifunctional isocyanate.

8. The particle of claim 1 wherein the particle is surface crosslinked with up to about 10,000 ppm of a surface crosslinking agent.

9. The particle of claim 8 wherein the surface crosslinking agent is selected from the group consisting of a polyhydroxy compound, a metal salt, a quaternary ammonium compound, a multifunctional epoxy compound, an alkylene carbonate, a polyaziridine, a haloepoxy, a polyamine, a polyisocyanate, and mixtures thereof.

10. The particle of claim 1 wherein the basic resin is lightly crosslinked.

11. The particle of claim 1 wherein at least 6% of the monomer units comprising the basic resin are basic monomer units.

12. The particle of claim 1 wherein the basic resin is selected from the group consisting of a poly(vinylamine), a poly(dialkylaminoalkyl (meth)acrylamide), a polymer prepared from the ester analog of an N-(dialkyamino(meth) acrylamide), a polyethylenimine, a poly (vinylguanidine), a poly (dimethyldialkylammonium hydroxide), a guanidine-modified polystyrene, a quaternized polystyrene, a quaternized poly(meth)acrylamide or ester analog thereof, poly (vinyl alcohol-co-vinylamine), and mixtures thereof.

13. The particle of claim 1 wherein the acidic resin contains a plurality of carboxylic acid, sulfonic acid, sulfuric acid, phosphonic acid, or phosphoric acid groups, or a mixture thereof.

14. The particle of claim 1 wherein at least 10% of the monomer units comprising the acidic resin are acidic monomer units.

15. The particle of claim 1 wherein the acidic resin is lightly crosslinked.

16. The particle of claim 1 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly (vinylsulfonic acid), a poly(vinylphosphoric acid), a poly (vinylsulfuric acid), a sulfonated polystyrene, and mixtures thereof.

17. The particle of claim 1 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

18. The particle of claim 17 wherein the poly (dialkylaminoalkyl (meth)acrylamide) comprises poly (dimethylaminoethyl acrylamide), poly (dimethylaminopropyl methacrylamide), or a mixture thereof.

19. The particle of claim 17 wherein the poly(acrylic acid) resin further contains strong acid moieties.

20. An article comprising a multicomponent superabsorbent particle of claim 1.

21. The article of claim 20, wherein the article is a diaper or a catamenial device.

22. A method of absorbing an aqueous medium comprising contacting the medium with a particle of claim 1.

23. A method of claim 22 wherein the aqueous medium contains electrolytes.

24. A method of claim 23 wherein the electrolyte-containing aqueous medium is selected from the group consisting of urine, saline, menses, and blood.

25. The particle of claim 1 wherein the basic resin comprises a strong basic resin, a weak basic resin, or a mixture thereof, and the acidic resin comprises a strong acidic resin, a weak acidic resin, or a mixture thereof.

26. A multicomponent superabsorbent particle comprising microdomains of at least one acidic water-absorbing resin dispersed throughout a continuous phase of at least one basic water-absorbing resin, said particle having a weight ratio of acidic resin to basic resin of about 90:10 to about 10:90, wherein the acidic resin has about 75% to 100% acid moieties present in the free acid form, and the basic resin has about 75% to 100% basic moieties present in a free base form.

27. A method of absorbing an aqueous medium comprising contacting the medium with a particle of claim 26.

28. The method of claim 27 wherein the aqueous medium contains electrolytes.

29. The method of claim 28 wherein the electrolyte-containing aqueous medium is selected from the group consisting of urine, saline, menses, and blood.

30. The particle of claim 26 wherein the basic resin comprises a strong basic resin, a weak basic resin, or a mixture thereof, and the acidic resin comprises a strong acidic resin, a weak acidic resin, or a mixture thereof.

31. The particle of claim 26 wherein the acidic resin is surface crosslinked with up to about 1% by weight of the particle of a surface crosslinking agent.

32. The particle of claim 26 wherein the particle is surface crosslinked with up to about 10,000 ppm of a surface crosslinking agent.

33. The particle of claim 26 wherein the basic resin is selected from the group consisting of a poly(vinylamine), a poly(dialkylaminoalkyl (meth)acrylamide), a polymer prepared from the ester analog of an N-(dialkylamino(meth) acrylamide), a polyethylenimine, a poly(vinylguanidine), a poly(dimethyldialkylammonium hydroxide), a guanidine-modified polystyrene, a quaternized polystyrene, a quaternized poly(meth)acrylamide or ester analog thereof, poly (vinyl alcohol-co-vinylamine), and mixtures thereof.

34. The particle of claim 26 wherein the acidic resin contains a plurality of carboxylic acid, sulfonic acid, sulfuric acid, phosphonic acid, or phosphoric acid groups, or a mixture thereof.

35. The particle of claim 26 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly (vinylsulfonic acid), a poly(vinylphosphoric acid), a poly (vinylsulfuric acid), a sulfonated polystyrene, and mixtures thereof.

36. The particle of claim 26 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

37. An article comprising a multicomponent superabsorbent particle of claim 26.

38. A multicomponent superabsorbent particle comprising microdomains of at least one basic water-absorbing resin and microdomains of at least one acidic water-absorbing resin dispersed throughout a continuous phase of a matrix resin,
said particle having a weight ratio of acidic resin to basic resin of about 90:10 to about 10:90, wherein the acidic resin has about 75% to 100% acid moieties present in the free acid form, and the basic resin has about 75% to 100% basic moieties present in a free base form.

39. The particle of claim 38 comprising 25% to 50%, by weight, of a matrix resin.

40. The particle of claim 38 wherein the matrix resin comprises a hydrophilic resin.

41. A method of absorbing an aqueous medium comprising contacting the medium with a particle of claim 38.

42. The method of claim 41 wherein the aqueous medium contains electrolytes.

43. The method of claim 42 wherein the electrolyte-containing aqueous medium is selected from the group consisting of urine, saline, menses, and blood.

44. The particle of claim 38 wherein the basic resin comprises a strong basic resin, a weak basic resins or a mixture thereof, and the acidic resin comprises a strong acidic resin, a weak acidic resin, or a mixture thereof.

45. The particle of claim 38 wherein the basic resin, acidic resin, or both, are surface crosslinked with up to about 1% by weight of the particle of a surface crosslinking agent.

46. The particle of claim 38 wherein the particle is surface crosslinked with up to about 10,000 ppm of a surface crosslinking agent.

47. The particle of claim 38 wherein the basic resin is selected from the group consisting of a poly(vinylamine), a poly(dialkylaminoalkyl (meth)acrylamide), a polymer prepared from the ester analog of an N-(dialkylamino(meth) acrylamide), a polyethylenimine, a poly(vinylguanidine), a poly(dimethyldialkylammonium hydroxide), a guanidine-modified polystyrene, a quaternized polystyrene, a quaternized poly(meth)acrylamide or ester analog thereof, poly (vinyl alcohol-co-vinylamine), and mixtures thereof.

48. The particle of claim 38 wherein the acidic resin contains a plurality of carboxylic acid, sulfonic acid, sulfuric acid, phosphonic acid, or phosphoric acid groups, or a mixture thereof.

49. The particle of claim 38 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly (vinylsulfonic acid), a poly(vinylphosphoric acid), a poly (vinylsulfuric acid), a sulfonated polystyrene, and mixtures thereof.

50. The particle of claim 38 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

51. An article comprising a multicomponent superabsorbent particle of claim 38.

52. A multicomponent superabsorbent particle comprising microdomains of at least one basic water-absorbing resin in intimate contact with microdomains of at least one acidic water-absorbing resin, said microdomains dispersed throughout said particle, and
said particle having a weight ratio of acidic resin to basic resin of about 90:10 to about 10:90, wherein the acidic resin has about 75% to 100% acid moieties present in the free acid form, and the basic resin has about 75% to 100% basic moieties present in a free base form.

53. The particle of claim 52 further comprising microdomains of a matrix resin in an amount of 0% to 50% by weight of the particle.

54. The particle of claim 52 consisting essentially of the microdomains of the acidic resin and the microdomains of the basic resin.

55. A method of absorbing an aqueous medium comprising contacting the medium with a particle of claim 52.

56. The method of claim 55 wherein the aqueous medium contains electrolytes.

57. The method of claim 56 wherein the electrolyte-containing aqueous medium is selected from the group consisting of urine, saline, menses, and blood.

58. The particle of claim 52 wherein the basic resin comprises a strong basic resin, a weak basic resin, or a mixture thereof, and the acidic resin comprises a strong acidic resin, a weak acidic resin, or a mixture thereof.

59. The particle of claim 52 wherein the acidic resin is surface crosslinked with up to about 1% by weight of the particle of a surface crosslinking agent.

60. The particle of claim 52 wherein the particle is surface crosslinked with up to about 10,000 ppm of a surface crosslinking agent.

61. The particle of claim 52 wherein the basic resin is selected from the group consisting of a poly(vinylamine), a poly(dialkylaminoalkyl (meth)acrylamide), a polymer prepared from the ester analog of an N-(dialkylamino(meth) acrylamide), a polyethylenimine, a poly(vinylguanidine), a poly(dimethyldialkylammonium hydroxide), a guanidine-modified polystyrene, a quaternized polystyrene, a quaternized poly(meth)acrylamide or ester analog thereof, poly (vinyl alcohol-co-vinylamine), and mixtures thereof.

62. The particle of claim 52 wherein the acidic resin contains a plurality of carboxylic acid, sulfonic acid, sulfuric acid, phosphonic acid, or phosphoric acid groups, or a mixture thereof.

63. The particle of claim 52 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, and mixtures thereof.

64. The particle of claim 52 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

65. An article comprising a multicomponent superabsorbent particle of claim 52.

66. A multicomponent superabsorbent particle comprising microdomains of a first water-absorbing resin dispersed throughout a continuous phase of a second water-absorbing resin, said particle having a weight ratio of first water-absorbing resin to second water-absorbing resin of about 90:10 to about 10:90, wherein the first and second water-absorbing resins have about 75% to 100% pendant moieties present in an unneutralized form.

67. The particle of claim 66 wherein the first resin comprises a basic water-absorbing resin, and the second resin comprises an acidic water-absorbing resin.

68. The particle of claim 67 wherein the basic resin comprises a strong basic resin, a weak basic resin, or a mixture thereof, and the acidic resin comprises a strong acidic resin, a weak acidic resin, or a mixture thereof.

69. The particle of claim 67 wherein the basic resin is selected from the group consisting of a poly(vinylamine), a poly(dialkylaminoalkyl (meth)acrylamide), a polymer prepared from the ester analog of an N-(dialkylamino(meth)acrylamide), a polyethylenimine, a poly(vinylguanidine), a poly(dimethyldialkylammonium hydroxide), a guanidine-modified polystyrene, a quaternized polystyrene, a quaternized poly(meth)acrylamide or ester analog thereof, poly(vinyl alcohol-co-vinylamine), and mixtures thereof.

70. The particle of claim 67 wherein the acidic resin contains a plurality of carboxylic acid, sulfonic acid, sulfuric acid, phosphonic acid, or phosphoric acid groups, or a mixture thereof.

71. The particle of claim 67 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, and mixtures thereof.

72. The particle of claim 67 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

73. The particle of claim 66 wherein the first resin comprises an acidic water-absorbing resin, and the second resin comprises a basic water-absorbing resin.

74. The particle of claim 73 wherein the basic resin is selected from the group consisting of a poly(vinylamine), a poly(dialkylaminoalkyl (meth)acrylamide), a polymer prepared from the ester analog of an N-(dialkylamino(meth)acrylamide), a polyethylenimine, a poly(vinylguanidine), a poly(dimethyldialkylammonium hydroxide), a guanidine-modified polystyrene, a quaternized polystyrene, a quaternized poly(meth)acrylamide or ester analog thereof, poly(vinyl alcohol-co-vinylamine), and mixtures thereof.

75. The particle of claim 73 wherein the acidic resin contains a plurality of carboxylic acid, sulfonic acid, sulfuric acid, phosphonic acid, or phosphoric acid groups, or a mixture thereof.

76. The particle of claim 73 wherein the acidic resin is selected from the group consisting of polyacrylic acid, a hydrolyzed starch-acrylonitrile graft copolymer, a starch-acrylic acid graft copolymer, a saponified vinyl acetate-acrylic ester copolymer, a hydrolyzed acrylonitrile polymer, a hydrolyzed acrylamide copolymer, an ethylene-maleic anhydride copolymer, an isobutylene-maleic anhydride copolymer, a poly(vinylphosphonic acid), a poly(vinylsulfonic acid), a poly(vinylphosphoric acid), a poly(vinylsulfuric acid), a sulfonated polystyrene, and mixtures thereof.

77. The particle of claim 73 wherein the basic resin comprises a poly(vinylamine), a poly(dialkylaminoalkyl (meth)acrylamide), a poly(vinylguanidine), a polyethylenimine, or a mixture thereof, and the acidic resin comprises poly(acrylic acid).

78. An article comprising a multicomponent superabsorbent particle of claim 66.

79. The article of claim 78, wherein the article is a diaper or a catamenial device.

80. A method of absorbing an aqueous medium comprising contacting the medium with a particle of claim 66.

81. A method of claim 80 wherein the aqueous medium contains electrolytes.

82. A method of claim 81 wherein the electrolyte-containing aqueous medium is selected from the group consisting of urine, saline, menses, and blood.

83. The particle of claim 66 wherein the first resin comprises an acidic water-absorbing resin, a basic water-absorbing resin, or a mixture thereof and the second resin comprises a matrix resin.

84. The particle of claim 66 wherein the first water-absorbing resin, second water-absorbing resin, or both, are surface crosslinked with up to about 1% by weight of the particle of a surface crosslinking agent.

85. The particle of claim 66 wherein the particle is surface crosslinked with up to about 10,000 ppm of a surface crosslinking agent.

* * * * *